US008104149B1

(12) United States Patent
McGarity

(10) Patent No.: US 8,104,149 B1
(45) Date of Patent: Jan. 31, 2012

(54) MONEY CLIP

(75) Inventor: Ronald M. McGarity, Savannah, GA (US)

(73) Assignee: Geraghty, LLC, Savannah, GA (US)

( * ) Notice: Subject to any disclaimer, the term of this patent is extended or adjusted under 35 U.S.C. 154(b) by 0 days.

(21) Appl. No.: 12/924,145

(22) Filed: Sep. 22, 2010

(51) Int. Cl.
B42F 1/02 (2006.01)
(52) U.S. Cl. ............... 24/558; 24/67.5; 24/565; 24/508; 24/513
(58) Field of Classification Search ............ 24/67.5, 24/513, 499, 500, 501, 511, 508, 557, 565, 24/558; 223/96, 93, 90
See application file for complete search history.

(56) References Cited

U.S. PATENT DOCUMENTS

| 1,151,556 | A | * | 8/1915 | Barney | 24/565 |
| 1,684,721 | A | * | 9/1928 | Wood | 24/501 |
| 4,716,634 | A | * | 1/1988 | Fan | 24/545 |
| 5,241,728 | A | * | 9/1993 | Hunter | 24/511 |
| 5,946,778 | A | | 9/1999 | McGarity | |
| 6,418,595 | B1 | * | 7/2002 | Shih | 24/536 |
| 6,988,296 | B1 | | 1/2006 | McGarity et al. | |

* cited by examiner

Primary Examiner — Robert J Sandy
Assistant Examiner — Abigail E Morrell
(74) Attorney, Agent, or Firm — Rodgers & Rodgers

(57) ABSTRACT

A money clip includes a pair of jaws joined together by means of a throat with a pair housings at least partially enveloping the jaws. A pair of operating levers are slidably mounted, respectively, in the housings with an elongated slot formed on the interior of each operating lever. A locking arm is attached to each jaw disposed and positioned to form an interlocking relationship between the jaw and respective operating lever.

7 Claims, 3 Drawing Sheets

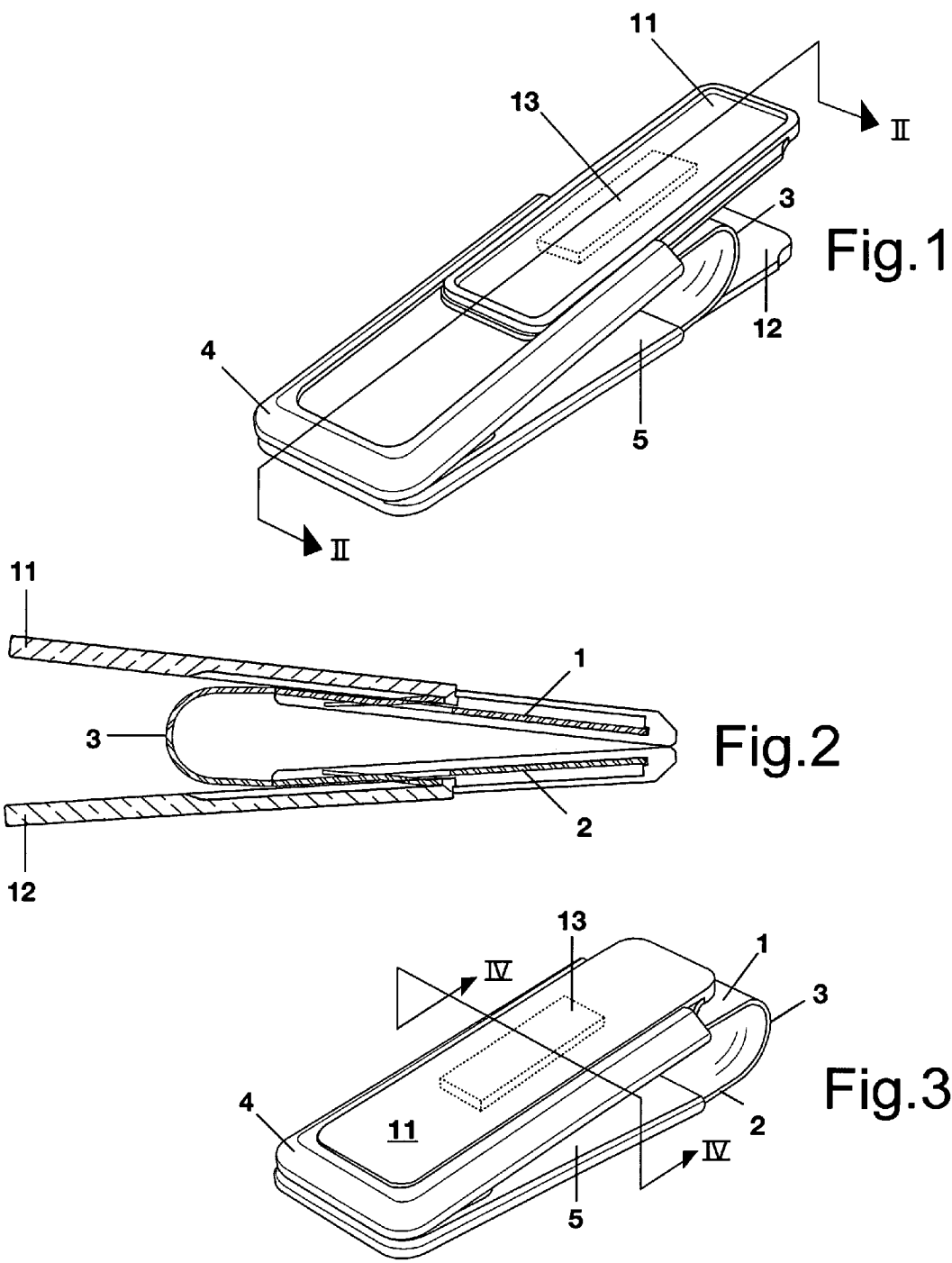

MONEY CLIP

BACKGROUND OF THE INVENTION

Devices to hold items such as paper currency, credit cards, drivers licenses etc. have been employed in many variations such as basic enlarged paper clips and standard binder clips which have foldable arms, all of which are well known. Advances in the art include money clips with retractable operating levers which are described in McGarity U.S. Pat. Nos. 5,946,778 and 6,988,296. Money clips with operating levers were a major advancement in that they allowed the clip to be easily and conveniently opened by squeezing the extended operating levers together and then retracting the levers to positions so that they are out of the way when not in use.

Since money clips with extendable and retractable levers include multiple slidable parts, they require precise manufacturing of the individual parts of the money clip and also require detailed and time-consuming assembly in order to produce an attractive and reliable clip. At times, excessive force is applied by a user when withdrawing the levers which can cause the levers to separate from the body of the clip.

SUMMARY OF THE INVENTION

By this invention, a money clip includes extendable operating levers which extend outwardly for the purpose of opening the money clip and retract inwardly in a compact fashion when not in use. The money clip embodies a spring clip having a pair of jaws for biasing the money clip in the closed position and with a pair of housings enveloping the jaws. The operating levers are slidably interconnected to the housings and a locking arm is struck from and attached to each jaw with the free end thereof disposed in an interlocking relationship with a slot formed on the interior of each operating lever.

BRIEF DESCRIPTION OF THE SEVERAL VIEWS OF THE DRAWINGS

In the drawings:

FIG. 1 is a perspective view of a money clip, according to this invention, with the operating levers in the extended positions;

FIG. 2 is a side elevational view taken along the line II-II in FIG. 1;

FIG. 3 is a perspective view of the money clip with the operating levers in a retracted condition;

DETAILED DESCRIPTION OF THE INVENTION

Figure 4:
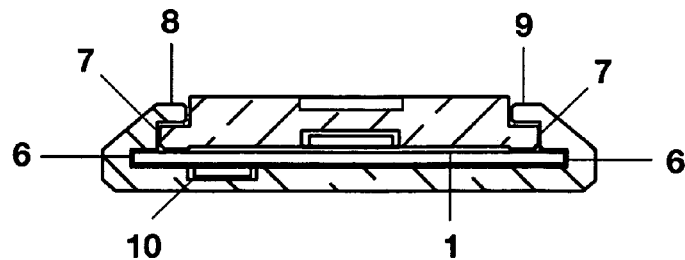
FIG. 4 is a cross-sectional view taken along the IV-IV in FIG. 3.

In the drawings and with particular reference to FIGS. 1-3, the money clip, according to this invention, is shown and includes a spring clip having upper and lower jaws 1 and 2 which are joined together by throat 3. As known in the art, throat 3 is spring-loaded so as to urge jaws 1 and 2 together and thereby provide the biasing force to hold the user's currency, credit cards and the like in a secure stored manner.

The money clip includes a pair of operating lever housings 4 and 5 which partially envelope, respectively, jaws 1 and 2. As shown in FIG. 4, each of the housings 4 and 5 has spaced elongated slots 6 and 7 with a pair of spaced elongated shoulders 8 and 9 disposed generally above and coextensive with slots 6 and 7. In addition, notch 10 is formed on the interior surface of each housing 4 and 5.

To complete the basic elements of the money clip, according to this invention, operating levers 11 and 12 are slidably receivable in housings 4 and 5, respectively. If desired, a radio frequency identification device (RFID) 13 may be embedded in one of the operating levers 11 or 12 and as shown in FIGS. 1 and 3. Also, in order to enhance the aesthetic appeal of the clip, decorative additions can be affixed to the operating levers such as precious stones, leather, plastic, rubber, wood and other like items.

Figure 8:
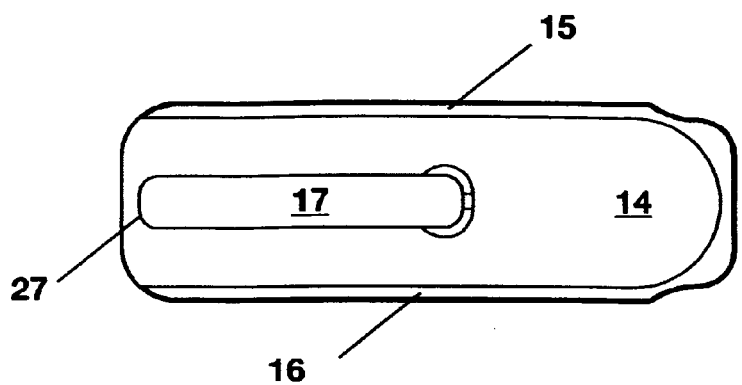
FIG. 8 is a plan view of the underside of the money clip operating lever.
Figure 9:
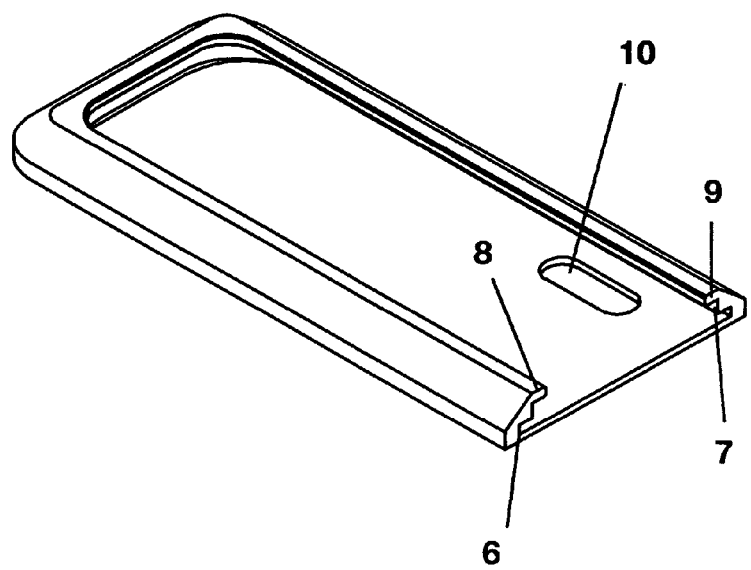
FIG. 9 is a perspective view of the money clip housing.

The details of operating levers 11 and 12 are shown in FIG. 8 wherein each includes base plate 14 having spaced flanges 15 and 16 extending along the side edges thereof. On the interior surface of base plate 14, elongated slot 17 is formed therein for the purpose of facilitating the frictional sliding movement of operating levers 11 and 12 and providing a stop mechanism when the levers are maneuvered to their operating positions.

Figure 5:
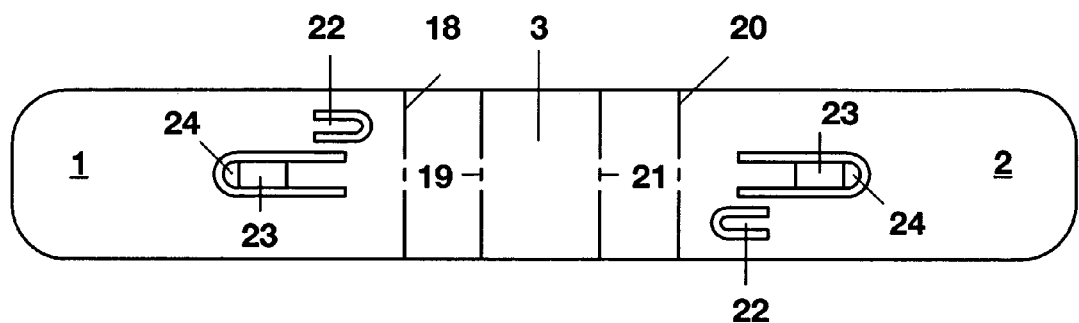
FIG. 5 is a plan view of the spring clip disposed in a flat condition.

The spring bias for the money clip is provided by means of the spring clip shown in the flat condition in FIG. 5. The spring clip includes bend lines 18 and 19 associated with upper jaw 1 and, likewise, bend lines 20 and 21 associated with lower jaw 2. In addition, each of the upper and lower jaws 1 and 2, includes locking tab 22 and locking arm 23 formed by any suitable cutting means such as laser, stamping and the like. Each locking arm 23 further includes locking tip 24 disposed on the free end of locking arm 23 and bendable along bearing line 25. Finally, locking arm 23 is bendable upwardly along bend line 26.

Figure 6:
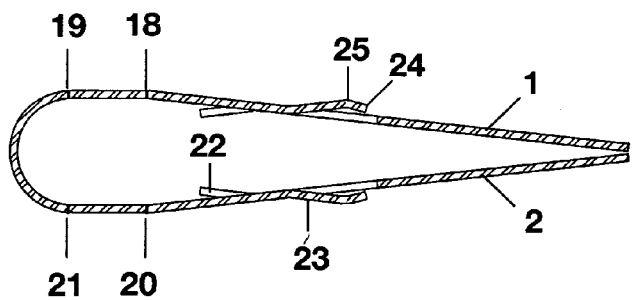
FIG. 6 is a sectional view taken along the line VI-VI in FIG. 7.
Figure 7:
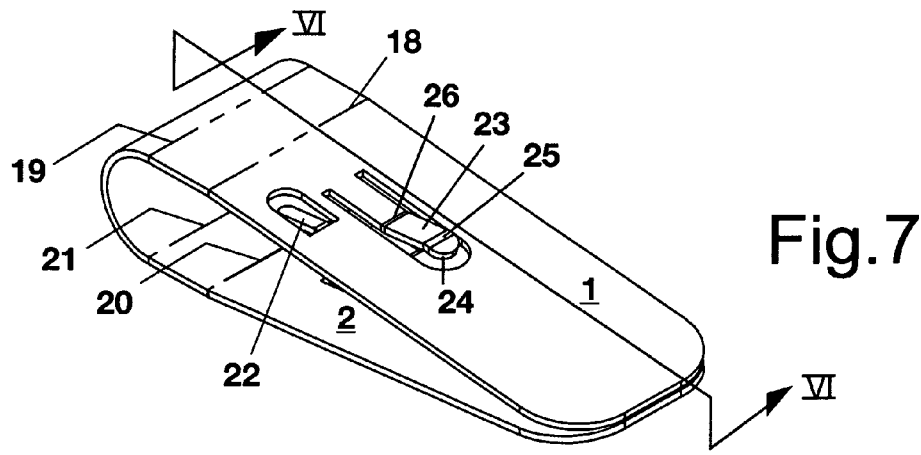
FIG. 7 is a perspective view of the spring clip disposed in the folded condition.

In order to form the money clip, according to this invention, initially it is necessary to fold the spring clip, shown in FIG. 5, such that the free ends of upper and lower jaws 1 and 2 are brought together to appear as shown in FIGS. 6 and 7 and then the spring clip is heat treated so that it is maintained in a permanent folded condition. Of course, heat-treating would be unnecessary if the clip is made of plastic or another non-metal material. Thereafter, locking tabs 22 are folded inwardly and locking arms 23 are folded outwardly with respect to upper and lower jaws 1 and 2. Simultaneously with this operation, throat 3 of the spring clip is folded to a slight degree along fold lines 18-21 and following this, locking tips 24 of each locking arm 23 are folded inwardly of the clip toward the respective jaw along bearing lines 25.

Then, upper and lower jaws 1 and 2 are separated a sufficient distance to allow upper and lower jaws 1 and 2 to be inserted into housings 4 and 5. This is accomplished by inserting jaws 1 and 2 into the respective housing 4 and 5 such that the jaw is inserted into the respective slot 6 of housings 4 and 5. As this occurs, locking tabs 22 are caused to drop into notches 10 of each housing 4 and 5 which, in effect, locks the housings onto the spring clip.

The final stage in assembling the money clip includes the insertion of operating levers 11 and 12 into the respective housings 4 and 5 so that flanges 15 and 16 slide under shoulders 8 and 9, respectively, and into slot 7 of each housing. Concurrently with this operation, locking arms 23, which are in the position shown in FIGS. 6 and 7, are forced to spring into slot 17 of each operating lever 11 and 12. The fully completed money clip then appears as shown in FIGS. 1, 2 and 3.

According to a feature of this invention, operating levers 11 and 12 are slidable within housings 4 and 5, respectively, and are completely prevented from inadvertent withdrawal from the housings when the levers are maneuvered outwardly into their operating positions. As operating levers 11 and 12 are moved outwardly of the money clip, bearing line 25 slides along the surface of slot 17 until the locking end 27 of slot 17 comes into abutting contact with locking tip 24. By this means, further withdrawal of operating levers 11 and 12 is not permitted no matter the amount of reasonable manual force applied to the operating levers. In addition, bearing line 25, being relatively thin, provides a minimum amount of metal-to-metal contact between locking arm 23 and slot 17 thereby creating minimal sliding resistance which is desirable as operating levers 11 and 12 are moved inwardly or outwardly of the money clip. Also, bend lines 18-21 provide added leverage for operating levers 11 and 12 when the money clip is opened.

Therefore, by this invention, a money clip is provided which has the advantage of retractable operating levers with a minimum of parts. Further, the money clip is economical to manufacture and can be assembled with efficiency and minimal complexity. Also, this invention is described in connection with money clips, it is equally adaptable for use in connection with other products such as surgical clamps, hand tools and various other types of clamping devices. This invention simplifies the manufacturing process, reduces overall costs and resolves the problem of operating levers being inadvertently pulled out of the clip.

The invention claimed is:

1. A clip comprising a pair of jaws, a throat interconnecting said jaws to urge said jaws toward each other, a pair of housings at least partially enveloping respectively said jaws, a pair of operating levers slidably mounted respectively in said housings, a slot formed on the interior of each of said operating levers; and a pair of locking arms attached respectively to said jaws and slidable in said slots.

2. The clip according to claim 1 wherein said locking arms are bendably attached to said jaws and a locking tip is formed on the free end of each locking arm.

3. The clip according to claim 2 wherein a locking end is formed on one end of each of said slots and adaptable to engage the respective one of said locking tips.

4. The clip according to claim 2 wherein said locking tip is bendably joined to said locking arm.

5. The clip according to claim 1 wherein a radio frequency identification device is embedded in one of said operating levers.

6. The clip according to claim 1 wherein multiple bend lines are formed in said throat.

7. The clip according to claim 1 wherein a notch is formed on the interior of each of said housings and a locking tab is bendably joined to each of said jaws and disposed in the respective one of said notches.

* * * * *